United States Patent
Dresher

(10) Patent No.: US 9,952,270 B2
(45) Date of Patent: Apr. 24, 2018

(54) ELECTRONIC DEVICES AND METHODS FOR ADDRESSING EXTERNAL ELECTROMAGNETIC FIELDS

(71) Applicant: Boston Scientific Scimed, Inc., Maple Grove, MN (US)

(72) Inventor: Russell P. Dresher, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 128 days.

(21) Appl. No.: 14/687,190

(22) Filed: Apr. 15, 2015

(65) Prior Publication Data
US 2015/0301096 A1 Oct. 22, 2015

Related U.S. Application Data

(60) Provisional application No. 61/980,117, filed on Apr. 16, 2014.

(51) Int. Cl.
| | | |
|---|---|---|
| G01R 29/10 | (2006.01) | |
| G01R 29/12 | (2006.01) | |
| A61B 1/005 | (2006.01) | |
| A61B 1/00 | (2006.01) | |

(52) U.S. Cl.
CPC ............ *G01R 29/12* (2013.01); *G01R 29/10* (2013.01); *A61B 1/00009* (2013.01); *A61B 1/0057* (2013.01)

(58) Field of Classification Search
CPC ........ G01R 29/10; G01R 29/12; G01R 29/26; A61B 1/00009; A61B 1/0057; A61B 1/00016
See application file for complete search history.

(56) References Cited

U.S. PATENT DOCUMENTS

| | | | | |
|---|---|---|---|---|
| 5,057,106 A | * | 10/1991 | Kasevich | A61B 18/18 600/549 |
| 5,521,605 A | * | 5/1996 | Koike | H01Q 1/244 343/702 |
| 5,653,677 A | * | 8/1997 | Okada | A61B 1/00016 348/E13.014 |

(Continued)

FOREIGN PATENT DOCUMENTS

JP  2003190081 A  *  7/2003

*Primary Examiner* — Julian Huffman
*Assistant Examiner* — Michael Konczal
(74) *Attorney, Agent, or Firm* — Bookoff McAndrews, PLLC

(57) ABSTRACT

An electronic device may include a shaft insertable into a target area, and an electronic component configured to generate a signal. The electronic component may be on or within the shaft. The electronic device may also include at least one antenna on or within the shaft. The electronic device may also include a receiver operatively coupled to the antenna. The receiver may monitor an electrical characteristic of the antenna to identify an effect of an electromagnetic field on the electrical characteristic of the antenna. The electronic device may also include a processor communicatively coupled to the receiver. At least one of the receiver and the processor may predict an effect of the electromagnetic field on the signal generated by the electronic component, based at least in part on the effect of the electromagnetic field on the electrical characteristic of the antenna.

20 Claims, 6 Drawing Sheets

(56) References Cited

U.S. PATENT DOCUMENTS

| | | | |
|---|---|---|---|
| 7,558,620 B2 * | 7/2009 | Ishibashi | A61B 1/00016 |
| | | | 128/903 |
| 8,177,712 B2 | 5/2012 | Fujimori et al. | |
| 2003/0163142 A1 * | 8/2003 | Paltieli | A61B 17/3403 |
| | | | 606/130 |
| 2009/0240108 A1 * | 9/2009 | Shimizu | A61B 1/041 |
| | | | 600/109 |

* cited by examiner

ELECTRONIC DEVICES AND METHODS FOR ADDRESSING EXTERNAL ELECTROMAGNETIC FIELDS

CROSS-REFERENCE TO RELATED APPLICATIONS

This application claims the benefit of priority from U.S. Provisional Application No. 61/980,117, filed on Apr. 16, 2014, which is incorporated by reference herein in its entirety.

TECHNICAL FIELD

Embodiments of the present disclosure relate to medical systems and methods for addressing electromagnetic fields.

BACKGROUND

An electronic device may send, receive, and/or store an electrical signal when in use. During use, the electronic device may be exposed to an external electromagnetic field. The external electromagnetic field may be produced by another electronic device being used simultaneously in the same vicinity as the electronic device. The electromagnetic field may couple to the electronic device, causing an electromagnetic disturbance in the signal. The electromagnetic disturbance may degrade the quality of the signal, rending the signal inaccurate or even unusable. Shielding may be added to the electronic device in an attempt to block the electromagnetic field, thereby reducing the probability of the electromagnetic disturbance occurring, and/or reducing the severity of the effect the electromagnetic disturbance may have on characteristics of the signal.

In a medical environment, multiple electronic medical devices may be used simultaneously in the same vicinity. One of the electronic devices may remain outside of the subject's body. Another of the electronic devices may be used to access internal areas of the subject's body having large openings, passages, and cavities. Adding shielding to the electronic device that remains outside of the subject's body, and/or the electronic device used to access large openings, passages, and cavities, may be useful for protecting those electronic devices from external electromagnetic fields.

However, for an electronic device used to image internal areas of a subject's body having small openings, passages, and cavities, adding shielding may not be a viable option because the increase in size associated with adding shielding may make the electronic device too large to fit in the small openings, passages, and cavities of the subject's body. In one such electronic device, an image signal may be sent, received, and/or stored by the electronic device when it is used. If the electronic device is exposed to an external electromagnetic field, causing an electromagnetic disturbance in the image signal, one or more characteristics of the image signal may be affected. For example, one or more characteristics of the image signal may be degraded. The degradation may result in the image signal producing a single defective pixel, multiple defective pixels, or no image at all, on a display. Reducing such degradation may improve the performance of the electronic device.

SUMMARY

According to aspects of the present disclosure, an electronic device may include a shaft insertable into a target area. The electronic device may also include an electronic component configured to generate a signal. The electronic component may be on or within the shaft. The electronic device may also include at least one antenna on or within the shaft. The electronic device may also include a receiver operatively coupled to the antenna. The receiver may monitor an electrical characteristic of the antenna to identify an effect of an electromagnetic field on the electrical characteristic of the antenna. The electronic device may also include a processor communicatively coupled to the receiver. At least one of the receiver and the processor may predict an effect of the electromagnetic field on the signal generated by the electronic component, based at least in part on the effect of the electromagnetic field on the electrical characteristic of the antenna.

In addition or alternatively, the electrical characteristic of the antenna may include at least one of current and voltage in the antenna; the electronic component may include an imaging device, and the signal may include image data obtained by the imaging device; the shaft may be a shaft of a medical endoscope insertable into a body cavity; the electronic component may include an imaging device at a distal end of the shaft; the antenna may include at least one of an end cap, ring, or articulation link at a distal end of the shaft, and the receiver may monitor at least one of current and voltage in at least one of the end cap, ring, or articulation link; the antenna may include at least one of a steering wire for bending the shaft, or a sheath wire forming part of a sheath of the shaft, and the receiver may monitor at least one of current and voltage in at least one of the steering wire or sheath wire; the processor may be configured to generate a signal when the value indicative of the electrical characteristic of the antenna is outside of a predetermined range of values; the signal generated by the processor may include at least one of a warning signal for display on a display device, a duplicate of the signal generated by the electronic component prior to the moment the value indicative of the electrical characteristic of the antenna fell outside the predetermined range, or a supplemental signal added to the signal generated by the electronic component; and/or the electronic device may include a display device for displaying the signal generated by the processor.

According to aspects of the present disclosure, an electronic system may include a first electronic device. The first electronic device may include a shaft insertable into a target area. The first electronic device may also include an electronic component configured to generate a signal. The electronic component may be on or within the shaft. The first electronic device may also include at least one antenna on or within the shaft. The first electronic device may also include a receiver operatively coupled to the antenna. The receiver may monitor an electrical characteristic of the antenna to identify an effect of an electromagnetic field on the electrical characteristic of the antenna. The first electronic device may also include a processor communicatively coupled to the receiver. At least one of the receiver and the processor may predict an effect of the electromagnetic field on the signal generated by the electronic component, based at least in part on the effect of the electromagnetic field on the electrical characteristic of the antenna. The electronic system may also include a second electronic device. Activation of the second electronic device may result in the second electronic device generating the electromagnetic field.

In addition or alternatively, the electronic component may include an imaging device, the signal may include image data obtained by the imaging device, and the effect of the electromagnetic field on the signal may include degradation of the image data; and/or the shaft may be a shaft of a medical endoscope insertable into a body cavity, and the imaging device may be at a distal end of the shaft.

According to aspects of the present disclosure, a method for predicting degradation of a signal in an electronic system may include generating a signal with an electronic component. The electronic component may be located on or within a distal portion of an electronic device. The method may also include monitoring at least one antenna located on the distal portion of the electronic device, with a receiver, to identify an effect of an electromagnetic field on an electrical characteristic of the antenna. The method may also include determining an effect of the electromagnetic field on the signal generated by the electronic component based on the effect of the electromagnetic field on the electrical characteristic of the antenna.

In addition or alternatively, the electrical characteristic of the antenna may be at least one of current and voltage in the antenna; the electronic component may be an imaging device, and the signal may include image data obtained by the imaging device; the effect of the electromagnetic field on the signal may be to degrade the signal by at least one of weakening the signal, interrupting the signal, and distorting the signal; the method may further include communicating a warning to a user of the electronic system when the monitored electrical characteristic exceeds a predetermined value; the method may further include altering the signal generated by the electronic component when the monitored electrical characteristic exceeds a predetermined value; and/or the method may further include repeating a previous signal generated by the electronic component when the monitored electrical characteristic exceeds a predetermined value.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Overview

According to aspects of the present disclosure, an electronic device may be provided with an antenna and a receiver for detecting an external electromagnetic field, identifying one or more characteristics of the external electromagnetic field, and/or mitigating the effect the external electromagnetic field may have on an electronic signal sent, received, and/or stored by the electronic device.

Exemplary Embodiments

Reference will now be made in detail to exemplary embodiments of the present disclosure described above and illustrated in the accompanying drawings.

The terms "proximal" and "distal" are used herein to refer to the relative positions of the components of an exemplary medical device. When used herein, "proximal" refers to a position relatively closer to the exterior of the body or closer to a user using the medical device. In contrast, "distal" refers to a position relatively further away from the user using the medical device, or closer to the interior of the body.

Figure 1:
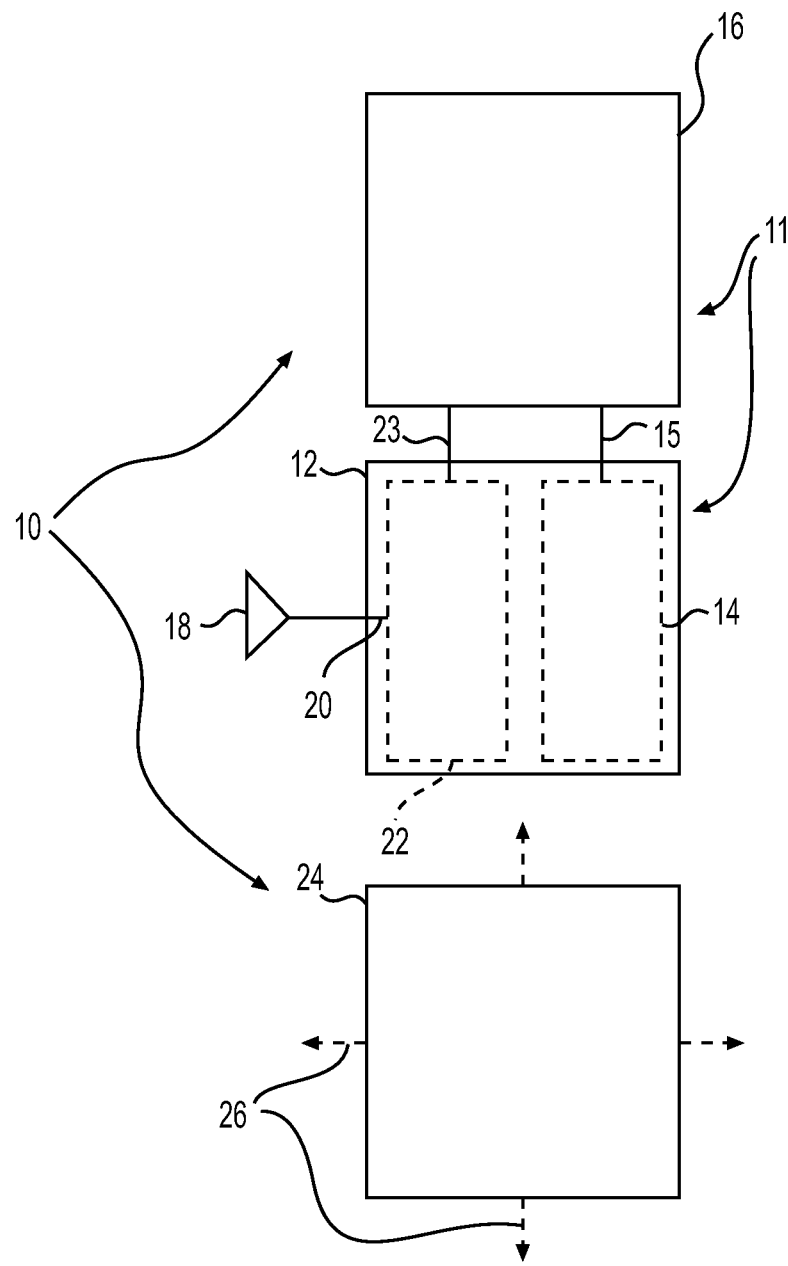
FIG. 1 is a schematic view of an exemplary electronic medical system, according to aspects of the present disclosure.

An electronic system 10, shown in FIG. 1, may be used to perform medical procedures. Electronic system 10 may include an electronic device or unit of electronic equipment 11. Electronic equipment 11 may include electronic tools 12 and 16. Electronic tool 12 may include an electronic component 14. Electronic component 14 may be operatively coupled to electronic tool 16 by an electrical connector 15. Electronic component 14 may generate one or more signals, and may relay signals to electronic tool 16 via connector 15. Electronic tool 16 may process received signals and generate an output.

Electronic tool 12 may also include an antenna 18 and a receiver 22. An antenna may include any suitable electrical device for converting electric power into electromagnetic waves, and/or for converting electromagnetic waves into a voltage at the antenna's terminals. Antenna 18 may be made of any suitable electrically-conductive material. For example, antenna 18 may be made of an electrically conductive metal. Antenna 18 may receive electric power from a power supply (not shown). Receiver 22 may be coupled to antenna 18 through antenna terminals 20.

The electric power for powering antenna 18 may come from receiver 22. Receiver 22 may monitor antenna 18. For example, receiver 22 may monitor current running through antenna 18. Additionally or alternatively, receiver 22 may monitor voltage at terminals 20. Receiver 22 may relay current and/or voltage information from antenna 18 to electronic tool 16 via an electrical connector 23 that operatively couples receiver 22 and electronic tool 16.

When antenna 18 is exposed to an external electromagnetic field, aspects of the antenna voltage and/or current may be affected. Through its monitoring of antenna 18, receiver 22 may detect the effects. The detected effects may provide information about the electromagnetic field to which antenna 18 is exposed. Receiver 22 may amplify the voltage at terminals 20 and/or current in antenna 18, and/or generate one or more signals based on the antenna voltage or current. Receiver 22 may relay the voltage, current, and/or signals to electronic tool 16 via electrical connector 23, to provide electronic tool 16 with information about the electromagnetic field.

System 10 may also include an electronic device or unit of electronic equipment 24. Electronic equipment 24 may include one or more electronic tools (not shown) having one or more electronic components (not shown). During operation of electronic system 10, activating electronic equipment 24 may result in electronic equipment 24 generating an electromagnetic field 26. Electromagnetic field 26 may couple to electronic component 14. In other words, electromagnetic field 26 may cause an electromagnetic disturbance in electronic component 14. The disturbance may interrupt, obstruct, or otherwise degrade the signals generated by electronic component 14 and/or relayed via connector 15, possibly resulting in electronic tool 16 receiving a degraded signal. Degradation may be characterized by a weakening of the signal, transformation of the signal, distortion of the signal, partial or total destruction of the signal, and/or any other altering of the signal resulting in the signal being inaccurate and/or unusable.

It is contemplated, however, that potential problems arising from the coupling of electromagnetic field 26 to electronic component 14 may be mitigated. For example, due to its proximity to electronic component 14, antenna 18 may be exposed to the same electromagnetic field 26 as electronic component 14 when electronic equipment 24 is activated. Thus, electromagnetic field 26 may affect voltage and/or current in antenna 18. Receiver 22 may obtain information about electromagnetic field 26 by monitoring the voltage and/or current in antenna 18. Receiver 22 may relay that information about electromagnetic field 26 to electronic tool 16 via electrical connector 23. It is contemplated that the relayed information may include voltage and/or current from antenna 18. Additionally or alternatively, the relayed information may include one or more values indicative of voltage and/or current of antenna 18. Additionally or alternatively, the relayed information may include information calculated by receiver 22 using the voltage and/or current of antenna 18.

Based at least in part on the information about electromagnetic field 26, the effect of electromagnetic field 26 on electronic component 14 may be predicted. The prediction may be made by at least one of receiver 22 and/or electronic tool 16. Using the prediction, electronic tool 16 may take steps, to address or mitigate the predicted effect. Exemplary steps are outlined in the description of the embodiment below.

Figure 2:
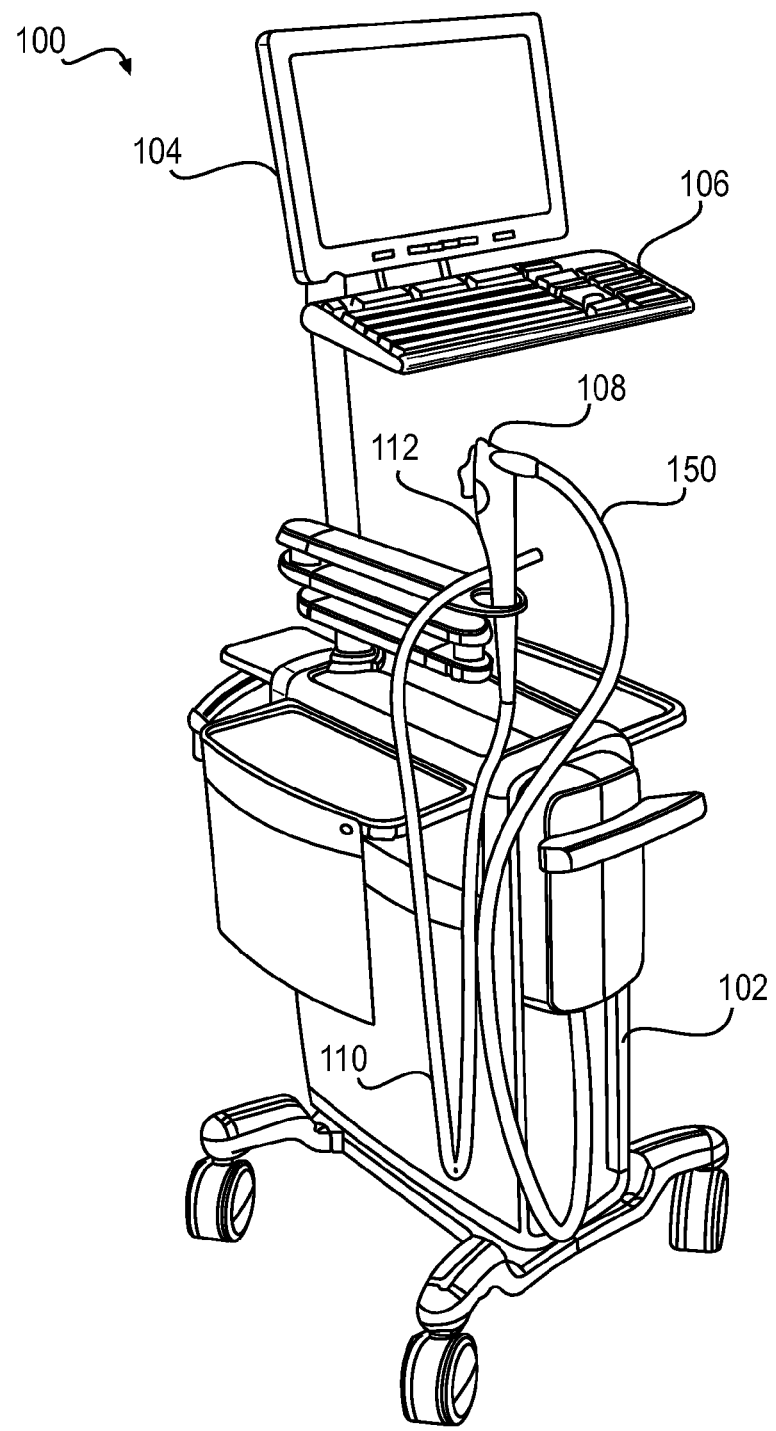
FIG. 2 is a perspective view of a unit of electronic medical equipment, according to aspects of the present disclosure.
Figure 3:
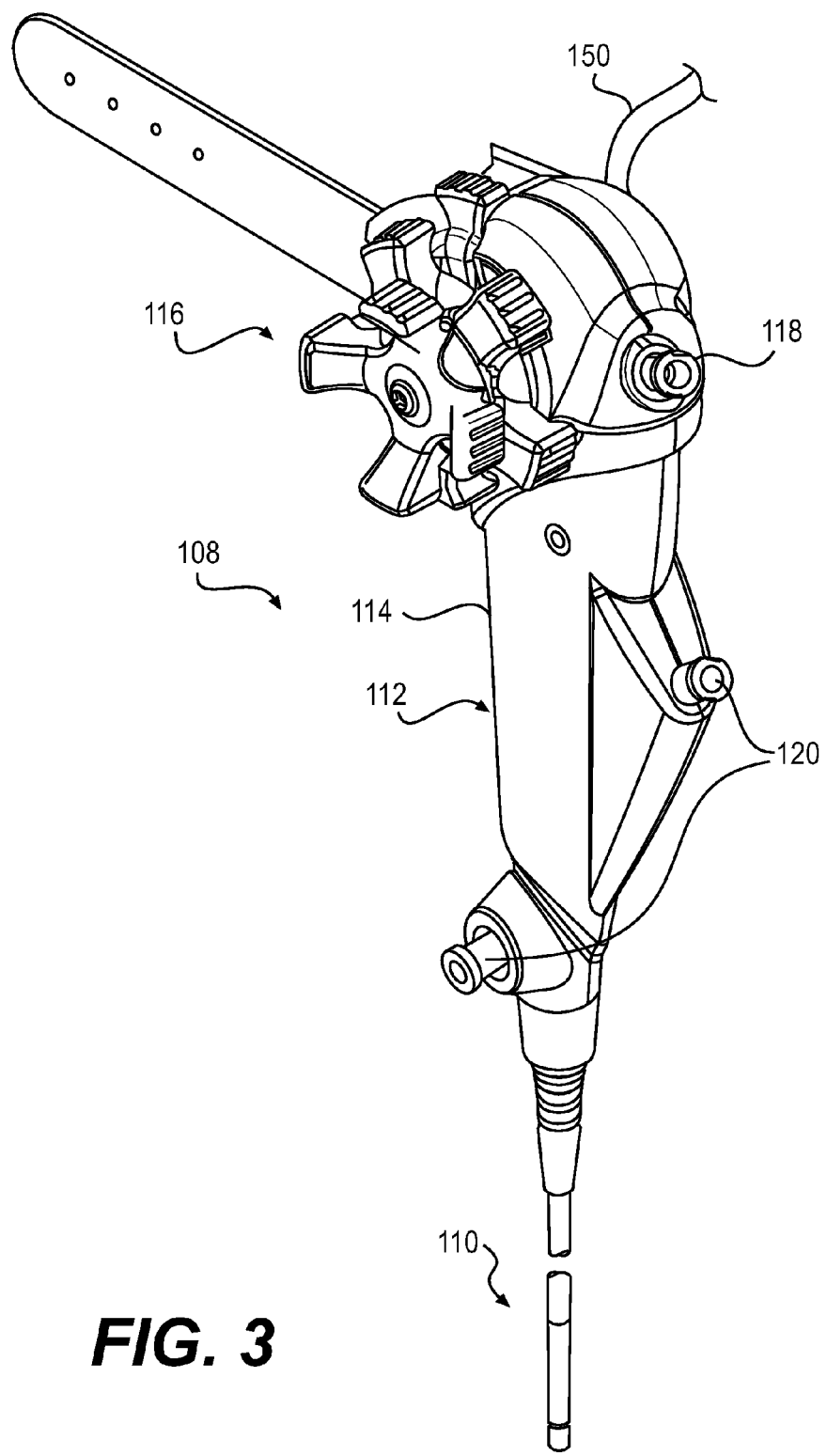
FIG. 3 is a perspective view of an electronic medical tool, according to aspects of the present disclosure.

In one embodiment, electronic equipment 11 may include endoscopic imaging equipment 100 (FIG. 2), electronic tool 12 may include an imaging endoscope 108, electronic component 14 may include an imaging assembly 138 (FIGS. 4A-4C), electrical connector 15 may include an imaging device transmission element 142, electronic tool 16 may include an image processor (not shown) in a control cabinet 102, antenna 18 may include one or more antennae discussed further below, receiver 22 may include a receiver 146 (FIG. 4E), and electrical connector 23 may include a receiver transmission element 147.

Imaging endoscope 108 may include a shaft 110 configured for insertion into a subject's body, and a handle assembly 112 coupled to a proximal end of shaft 110. Handle assembly 112 may include a handle housing 114. Handle assembly 112 may also include a steering mechanism 116. Steering mechanism 116 may control deflection of the distal end of shaft 110 by tensioning steering wires 128a-128d extending between steering mechanism 116 and the distal end of shaft 110. For example, steering mechanism 116 may include two rotatable knobs that may be coupled to pulleys configured to move steering wires 128a-128d, for four-way steering of the shaft distal end in the up/down direction and in the right/left direction. Handle assembly 112 may also include one or more ports 118 and 120 for providing access to channels 132a-132d running along the length of shaft 110. Exemplary ports may include a working channel port for receiving tools, an imaging device port, and an irrigation/suction port.

Imaging assembly 138 may include an imaging device 140 positioned at a distal end of shaft 110. Imaging device may be any suitable camera assembly, such as a CMOS sensor, and may be configured to obtain image data of a target area in a subject's body within its field of view. Imaging device 140 may generate one or more image signals based on the obtained image data. Imaging assembly 138 may also include imaging device transmission element 142. Imaging device 140 may relay image signals through shaft 110 and handle assembly 112 to control cabinet 102 via imaging device transmission element 142. Imaging device transmission element 142 may be received in an endoscope connection cable 150 coupling handle assembly 112 to control cabinet 102. Control cabinet 102 may use the received image signals to generate outputs, such as images, for showing on a display device 104. Display device 104 may include any suitable video screen or monitor.

Electronic equipment 24 may any medical device that may emit an electromagnetic field. For example, electronic equipment 24 may include an electrohydraulic lithotripter. The electrohydraulic lithotripter may be used for stone fragmentation in a subject's body. The electrohydraulic lithotripter may include a probe containing one or more electrodes. When activated, an electric current may energize the electrode, creating a spark at the end of the probe. The user may use imaging endoscope 108 to help guide electrohydraulic lithotripter 24 to a target area. In one embodiment, electrohydraulic lithotripter 24 may be inserted through one of channels 132a-132d of shaft 110 and out the distal end of a distal end cap 122 of endoscope 108.

When activated, electrohydraulic lithotripter 24 may emit electromagnetic field 26. Imaging assembly 138 may be exposed to electromagnetic field 26. Electromagnetic field 26 may couple to imaging assembly 138. That coupling may interfere with the operation of imaging assembly 138. For example, the coupling may degrade the image signal generated by imaging device 140 and/or relayed by imaging device transmission element 142. If left unaddressed, the degraded image signal may result in inaccurate output images, or no output images at all, showing up on display device 104. Without accurate output images, a user may have difficulty visualizing, and therefore performing, a procedure. This undesired outcome may be mitigated using antenna 18, receiver 146, and the image processor of control cabinet 102.

Receiver 146 may be housing in handle housing 114 (FIG. 4E), or in control cabinet 102. Receiver 146 may monitor electrical characteristics of antenna 18. For example, receiver 146 may monitor current running through antenna 18 between its terminals 20, and/or voltage at terminals 20. When electromagnetic field 26 is present, it may affect the current and/or voltage in antenna 18. Receiver 146 may relay the current and/or voltage to the image processor in control cabinet 102. Control cabinet 102 may process the current and/or voltage into a value, signal, and/or output. Additionally or alternatively, receiver 146 may process the current and/or voltage into a value, signal, and/or output, and relay the value, signal, or output to control cabinet 102.

Processing the current and/or voltage may include, for example, determining one or more characteristics of electromagnetic field 26 based on the current and/or voltage when antenna 18 is exposed to electromagnetic field 26. Processing the current and/or voltage may also include determining an effect electromagnetic field 26 may have on imaging assembly 138. For example, processing may include determining the effect of electromagnetic field 26 on imaging device 140 and/or imaging device transmission element 142. Determining the effect may include comparing a characteristic of electromagnetic field 26 to a value known to have a corresponding effect on imaging assembly 138. If the characteristic of electromagnetic field 26 matches the known value, or exceeds the known value, it is likely that electromagnetic field 26 is having or will have an effect on imaging assembly 138 that corresponds to the known value. Additionally or alternatively, processing the current and/or voltage may include running a value indicative of the current and/or voltage through an algorithm. The algorithm may accept the value as an input, perform a calculation on the input, and produce an output indicative of a predicted effect that electromagnetic field 26 may have on imaging assembly 138.

If the predicted effect is indicative of degradation of the image signal in imaging assembly 138, mitigating steps may be taken. For example, control cabinet 102 may relay an alert or warning signal to display device 104, to provide the user with notice that the output image may not be accurate due to degradation of the image signal. Additionally or alternatively, control cabinet 102 may cause display device 104 to display whatever output image was showing prior to occurrence of degradation of the image signal. This freezing of the output image may be achieved by, for example, repeating the last accurate image signal. Additionally or alternatively, control cabinet 102 may modify the output image signal to supplement or fix the degraded image signal, leading to a more accurate output image being displayed on display device 104. Other suitable actions may also be taken. The type of action taken may, for example, depend on the severity of predicted degradation of the image signal. Once electromagnetic field 26 is removed, the alert or warning may cease, the output image on display device 104 may be unfrozen, and/or supplementing or fixing of the image signal may cease. Endoscopic imaging equipment 100 may return to normal operation.

It should be understood that, to the extent an electronic device in imaging electronic equipment 100 may also produce its own electromagnetic field when activated, its own electromagnetic field may also be sensed by antenna 18. Its own electromagnetic field may be recognized by receiver 146 and/or control cabinet 102 as a baseline event. Receiver 146 and/or control cabinet 102 may consider only an event other than the baseline event when predicting degradation of the image signal. Alternatively, the baseline event may be considered in combination with electromagnetic field 26 to help predict degradation of the image signal.

Figure 4A:
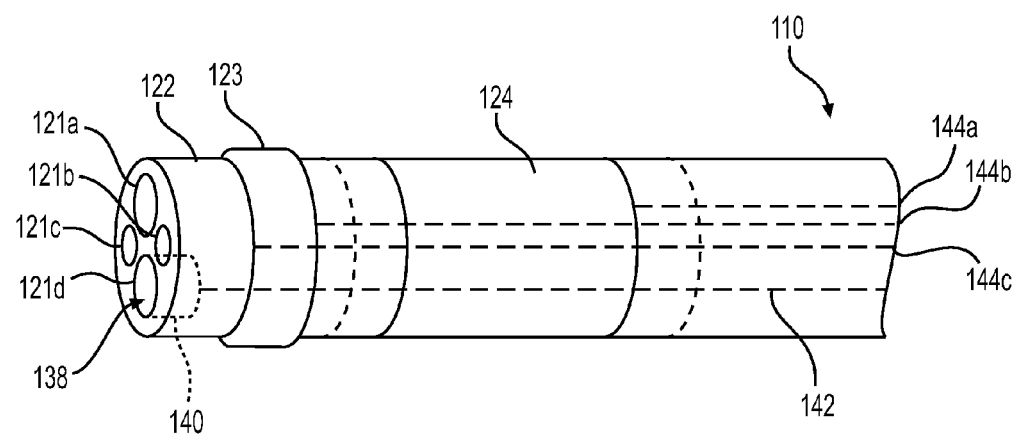
FIG. 4A is an enlarged view of a portion of an electronic medical tool, according to aspects of the present disclosure.

FIGS. 4A-4D show aspects of antenna 18. As shown in FIG. 4A, shaft 110 may include an outer sheath 124. Shaft 110 may also include a distal end cap 122 having openings or ports 121a-121d. Port 121d may receive imaging device 140. Shaft 110 may also include a distal ring 123. Distal ring 123 may assist with coupling outer sheath 124 to distal end cap 122. Shaft 110 may also include a reinforcement sheath 126 made of a plurality of struts or woven wires 127. Shaft 100 may also include one or more steering cables formed by one or more of wires 128a-128d and protective sheathing 129. Shaft 100 may also include an articulation joint 133, particularly at a distal end of shaft 100, to articulate the distal end. Articulation joint 133 may include one or more articulation links 134, and one or more springs 136 coupled to articulation links 134 to bias the articulation links into a straight-line configuration.

Antenna 18 may include a portion of outer sheath 124 and an antenna transmission element 144a (FIG. 4A). Outer sheath 124 may include an electrically-conductive portion. For example, at least a portion of outer sheath 124 may be made of an electrically-conductive metal. Additionally or alternatively, an electrically-conductive metal strip or other element (not shown) may be added to outer sheath 124. Additionally or alternatively, the electrically-conductive portion may run through outer sheath 124, such as through a wall of the outer sheath 124 between its interior and exterior surfaces. Antenna transmission element 144a may include, for example, one or more metallic wires for conducting electrical current. Antenna transmission element 144a may be coupled on its proximal end (terminal) to receiver 146, and on its distal end to the electrically-conductive portion of outer sheath 124. Current may flow through antenna transmission element 144a and the electrically-conductive portion of outer sheath 124. Through its connection to the proximal end of antenna transmission element 144a, receiver 146 may monitor current and/or voltage in antenna transmission element 144a and the electrically-conductive portion of outer sheath 124. It is also contemplated that antenna 18 may include antenna transmission element 144a alone, without requiring an electrically conductive portion of outer sheath 124.

Figure 4B:
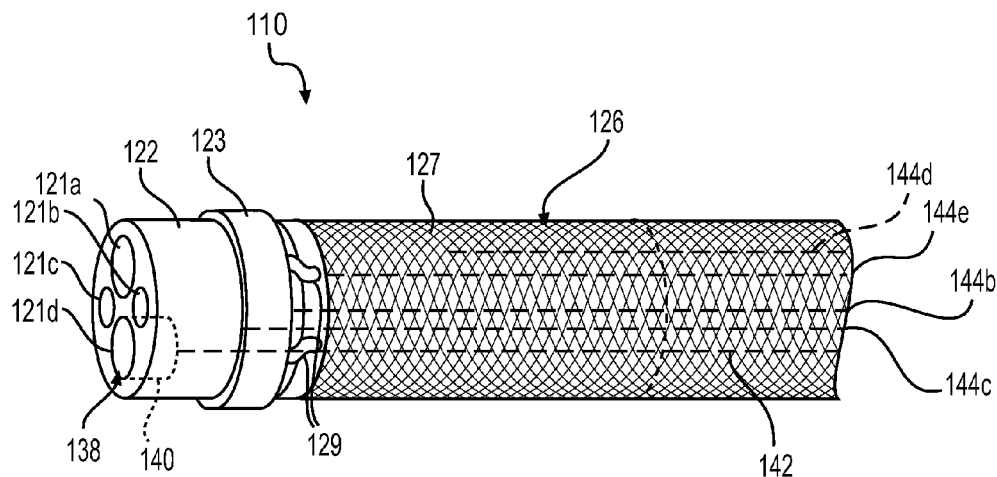
FIG. 4B is an enlarged view of a portion of an electronic medical tool, according to aspects of the present disclosure.
Figure 4C:
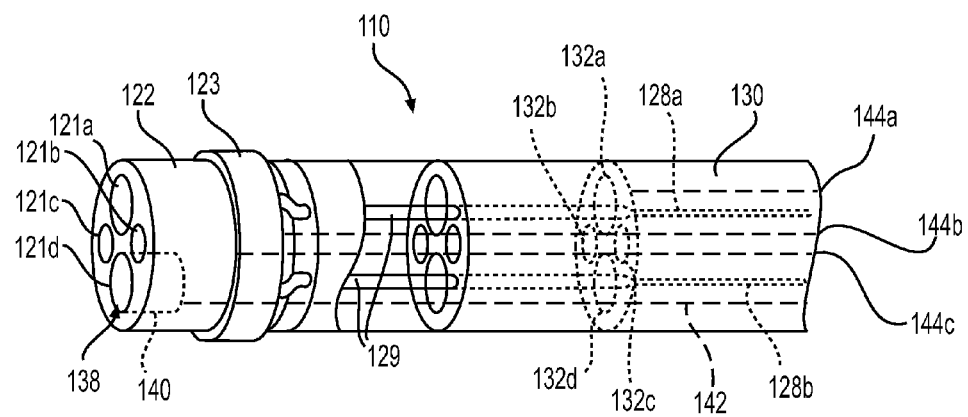
FIG. 4C is an enlarged view of a portion of an electronic medical tool, according to aspects of the present disclosure.

Additionally or alternatively, antenna 18 may include a portion of distal ring 123, and an antenna transmission element 144b (FIGS. 4A-4C). Distal ring 123 may include an electrically-conductive portion. For example, at least a portion of distal ring 123 may be made of an electrically-conductive metal. Additionally or alternatively, an electrically-conductive metal strip or other element (not shown) may be added to distal ring 123. Additionally or alternatively, the electrically-conductive portion may run through distal ring 123, such as through a wall of the distal ring 123 between its interior and exterior surfaces. Antenna transmission element 144b may include one or more metallic wires similar to antenna transmission element 144a. Antenna transmission element 144b may be coupled on its proximal end (terminal) to receiver 146, and on its distal end to the electrically-conductive portion of distal ring 123. Current may flow through antenna transmission element 144b and the electrically-conductive portion of distal ring 123. Through its connection to the proximal end (terminal) of antenna transmission element 144b, receiver 146 may monitor current and/or voltage in antenna transmission element 144b and the electrically-conductive portion of distal ring 123. It is also contemplated that antenna 18 may include antenna transmission element 144b alone, without requiring an electrically conductive portion of distal ring 123.

Additionally or alternatively, antenna 18 may include a portion of distal end cap 122, and an antenna transmission element 144c (FIGS. 4A-4C). Distal end cap 122 may include an electrically-conductive portion. For example, at least a portion of distal end cap 122 may be made of an electrically-conductive metal. Additionally or alternatively, an electrically-conductive metal strip or other element (not shown) may be added to distal end cap 122. Additionally or alternatively, the electrically-conductive portion may run through distal end cap 122, such as through a wall of distal end cap 122 between its interior and exterior surfaces. Antenna transmission element 144c may include one or more metallic wires similar to antenna transmission element 144a. Antenna transmission element 144c may be coupled on its proximal end (terminal) to receiver 146, and on its distal end to the electrically-conductive portion of distal end cap 122. Current may flow through antenna transmission element 144c and the electrically-conductive portion of distal end cap 122. Through its connection to the proximal end (terminal) of antenna transmission element 144c, receiver 146 may monitor current and/or voltage in antenna transmission element 144c and the electrically-conductive portion of distal end cap 122. It is also contemplated that antenna 18 may include antenna transmission element 144c alone, without requiring the electrically conductive portion of distal end cap 122.

Additionally or alternatively, antenna 18 may include a portion of reinforcement sheath 126, and an antenna transmission element 144d (FIG. 4B). Reinforcement sheath 126 may include an electrically-conductive portion. For example, at least a portion of reinforcement sheath 126 may be made of an electrically-conductive metal. In one embodiment, reinforcement sheath 126 may be made of woven wires or struts 127, at least one of which may be electrically-conductive. Additionally or alternatively, an electrically-conductive metal strip or other element (not shown) may be added to reinforcement sheath 126. Antenna transmission element 144d may include one or more metallic wires similar to antenna transmission element 144a. Antenna transmission element 144d may be coupled on its proximal end (terminal) to receiver 146, and on its distal end to the electrically-conductive portion of reinforcement sheath 126. Current may flow through antenna transmission element 144d and the electrically-conductive portion of reinforcement sheath 126. Through its connection to the proximal end (terminal) of antenna transmission element 144d, receiver 146 may monitor current and/or voltage in antenna transmission element 144d and the electrically-conductive portion of reinforcement sheath 126. It is also contemplated that antenna 18 may include antenna transmission element 144d alone, without requiring an electrically conductive portion of reinforcement sheath 126.

Additionally or alternatively, antenna 18 may include a portion of one or more of steering wires 128a-128d (FIGS. 4B, 4C, and 4E), and an antenna transmission element 144e. Antenna transmission element 144e may be one of steering wires 128a-128d. Steering wires 128-128d may be electrically-conductive. Steering wires 128a-128d may be coupled on their proximal ends (terminals) to receiver 146, and on their distal ends to distal end cap 122, distal ring 123, and/or articulation joint 133. Current may flow through one or more of steering wires 128a-128d. Through its connection to the proximal end (terminal) of one or more of steering wires 128a-128d, receiver 146 may monitor current and/or voltage therein.

Figure 4D:
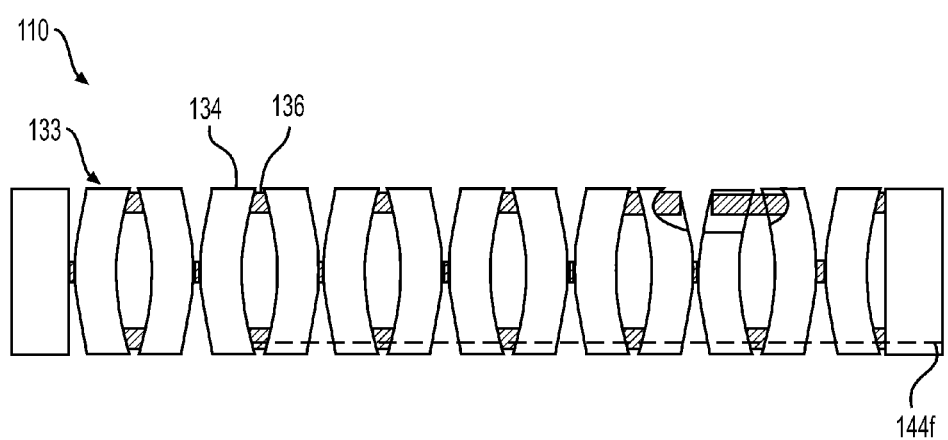
FIG. 4D is an enlarged view of a portion of an electronic medical tool, according to aspects of the present disclosure.

Additionally or alternatively, antenna 18 may include a portion of articulation link 134 and/or spring 136, and an antenna transmission element 144f (FIG. 4D). Articulation link 134 and/or spring 136 may include an electrically conductive portion. For example, at least a portion of articulation link 134 and/or spring 136 may be made of an electrically-conductive metal. Additionally or alternatively, an electrically conductive metal strip or other element may be added to articulation link 134 and/or spring 136. Additionally or alternatively, the electrically-conductive portion may run through a wall of articulation link 134 between its interior and exterior surfaces. Antenna transmission element 144f may include one or more metallic wires similar to antenna transmission element 144a. Antenna transmission element 144f may be coupled on its proximal end (terminal) to receiver 146, and on its distal end to the electrically-conductive portion of articulation link 134 and/or spring 136. Current may flow through antenna transmission element 144f and the electrically-conductive portion of articulation link 134 and/or spring 136. Through its connection to the proximal end (terminal) of antenna transmission element 144f, receiver 146 may monitor current and/or voltage in antenna transmission element 144f and the electrically-conductive portion of articulation link 134 and/or spring 136. It is also contemplated that antenna 18 may include antenna transmission element 144f alone, without requiring an electrically conductive portion of articulation link 134 and/or spring 136.

Figure 4E:
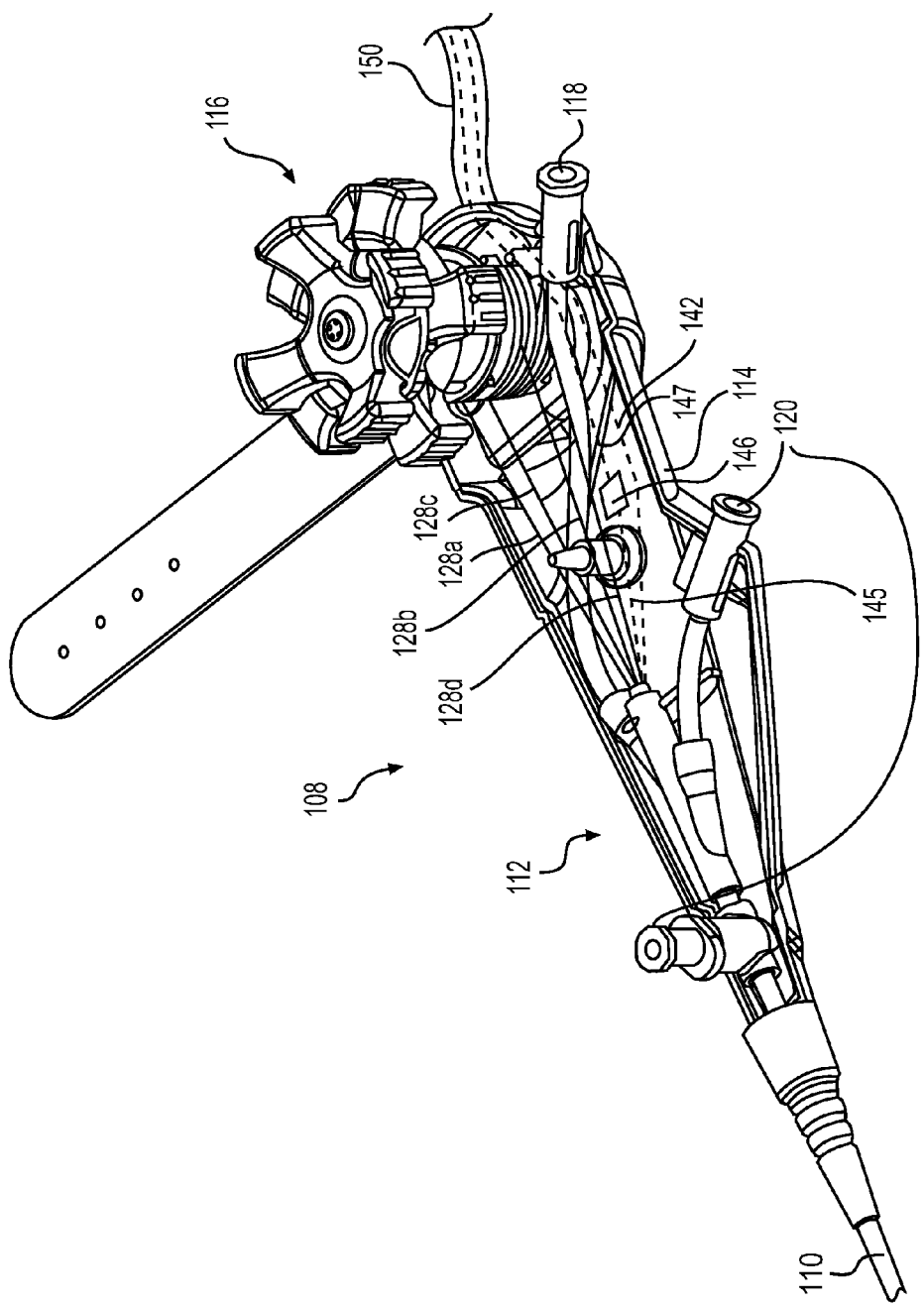
FIG. 4E is an enlarged view of a portion of an electronic medical tool, according to aspects of the present disclosure.

As shown in FIG. 4E, an antenna transmission element 145, which may include one or more of antenna transmission elements 144a-144d, and 144f, may extend through shaft 110 and into handle assembly 112 to couple antenna 18 to receiver 146. It is contemplated that antenna transmission elements 144a-144d and 144f may extend through one or more of channels 132a-132d in shaft 110, or any other suitable openings or lumens in shaft 110.

Any aspect set forth in any embodiment may be used with any other embodiment set forth herein. Every device and apparatus set forth herein may be used in any suitable medical procedure, may be advanced through any suitable body lumen and body cavity, and may be used for treatment of any suitable body portion. For example, the apparatuses and methods described herein may be used in any natural body lumen or tract, including those accessed orally, vaginally, or rectally.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

I claim:

1. An electronic device, comprising:
   an endoscope shaft having a distal end portion insertable into a target area;
   an electronic component configured to generate a data signal, wherein the electronic component is on or within at least the distal end portion of the endoscope shaft;
   a wire configured to conduct the data signal generated by the electronic component proximally through the endoscope shaft;
   at least one antenna on or within at least the distal end portion of the endoscope shaft, the antenna being spaced apart from the wire by a gap;
   a receiver operatively coupled to the antenna, wherein the receiver monitors an electrical characteristic of the antenna to identify an effect of an electromagnetic field on the electrical characteristic of the antenna; and
   a processor communicatively coupled to the receiver, wherein at least one of the receiver and the processor determines an effect of the electromagnetic field on the data signal generated by the electronic component, based at least in part on the effect of the electromagnetic field on the electrical characteristic of the antenna, and the processor modifies the data signal based at least in part on the determined effect to reduce the effect of the electromagnetic field on the data signal.

2. The electronic device of claim 1, wherein the electrical characteristic of the antenna is at least one of current and voltage in the antenna.

3. The electronic device of claim 1, wherein the electronic component includes an imaging device, and the data signal includes image data obtained by the imaging device.

4. The electronic device of claim 1, wherein the distal end portion of the endoscope shaft includes at least one of an external conductive end cap, an external conductive ring, or an internal conductive articulation link, wherein the at least one of the end cap, ring, or articulation link is part of the antenna, and wherein the receiver monitors at least one of current and voltage in the at least one of the end cap, ring, or articulation link.

5. The electronic device of claim 1, wherein the distal end portion of the endoscope shaft includes at least one of a steering wire for bending the endoscope shaft, or a sheath wire forming part of a sheath of the endoscope shaft, wherein the at least one of the steering wire or sheath wire is part of the antenna, and wherein the receiver monitors at least one of current and voltage in at least one of the steering wire or sheath wire.

6. The electronic device of claim 1, wherein the processor is configured to generate a signal when the value indicative of the electrical characteristic of the antenna is outside of a predetermined range of values.

7. The electronic device of claim 6, wherein the signal generated by the processor includes at least one of a duplicate of the data signal generated by the electronic component prior to the moment the value indicative of the electrical characteristic of the antenna fell outside the predetermined range, or a supplemental signal added to the data signal generated by the electronic component.

8. The electronic device of claim 6, further including a display device for displaying the signal generated by the processor.

9. The electronic device of claim 1, wherein a central longitudinal axis of the antenna is radially offset from a central longitudinal axis of the endoscope shaft.

10. The electronic device of claim 1, wherein at least a portion of the antenna surrounds at least a portion of the electronic component.

11. The electronic device of claim 1, wherein the electronic component includes an imaging assembly, the imaging assembly includes a distal imaging device and the wire, and wherein at least a portion of the antenna surrounds at least one of the distal imaging device and the wire.

12. An electronic system, comprising:
a first electronic device, including:
an endoscope shaft insertable into a target area,
an electronic component configured to generate a data signal, wherein the electronic component is on or within the endoscope shaft,
a wire configured to conduct the data signal generated by the electronic component proximally through the endoscope shaft;
at least one antenna on or within the endoscope shaft, wherein the antenna extends longitudinally alongside the electronic component on or within the endoscope shaft,
a receiver operatively coupled to the antenna, wherein the receiver monitors an electrical characteristic of the antenna to identify an effect of an electromagnetic field on the electrical characteristic of the antenna, and
a processor communicatively coupled to the receiver, wherein at least one of the receiver and the processor determines an effect of the electromagnetic field on the data signal generated by the electronic component, based at least in part on the effect of the electromagnetic field on the electrical characteristic of the antenna, and the processor modifies the data signal based at least in part on the determined effect to reduce the effect of the electromagnetic field on the data signal; and
a second electronic device, wherein activation of the second electronic device results in the second electronic device generating the electromagnetic field.

13. The electronic system of claim 12, wherein the electronic component includes an imaging device, the data signal includes image data obtained by the imaging device, and the effect of the electromagnetic field on the data signal is degradation of the image data.

14. A method for predicting degradation of a data signal in an electronic system, the method comprising:
generating the data signal with an electronic component, the electronic component being located on or within at least a distal portion of a bendable endoscope shaft of an electronic device;
transmitting the data signal through a wire in the bendable endoscope shaft;
monitoring at least one antenna located on at least the distal portion of the bendable endoscope shaft, with a receiver, to identify an effect of an electromagnetic field on an electrical characteristic of the antenna;
determining an effect of the electromagnetic field on the data signal generated by the electronic component based on the effect of the electromagnetic field on the electrical characteristic of the antenna; and
modifying the data signal based at least in part on the determined effect to reduce the effect of the electromagnetic field on the data signal.

15. The method of claim 14, wherein the electrical characteristic of the antenna is at least one of current and voltage in the antenna.

16. The method of claim 14, wherein the electronic component includes an imaging device, and the data signal includes image data obtained by the imaging device.

17. The method of claim 16, wherein the effect of the electromagnetic field on the data signal is to degrade the signal by at least one of weakening the data signal, interrupting the data signal, and distorting the data signal.

18. The method of claim 14, further including communicating a warning to a user of the electronic system when the monitored electrical characteristic exceeds a predetermined value.

19. The method of claim 14, further including altering the data signal generated by the electronic component when the monitored electrical characteristic exceeds a predetermined value.

20. The method of claim 14, further including repeating a previous data signal generated by the electronic component when the monitored electrical characteristic exceeds a predetermined value.

* * * * *